(12) United States Patent
Doan (10) Patent No.: US 6,956,210 B2
(45) Date of Patent: Oct. 18, 2005

(54) METHODS FOR PREPARING SAMPLES FOR ATOM PROBE ANALYSIS

(75) Inventor: Trung T. Doan, Pflugerville, TX (US)

(73) Assignee: Micron Tchnology, Inc., Boise, ID (US)

(*) Notice: Subject to any disclaimer, the term of this patent is extended or adjusted under 35 U.S.C. 154(b) by 0 days.

(21) Appl. No.: 10/687,111

(22) Filed: Oct. 15, 2003

(65) Prior Publication Data

US 2005/0082475 A1 Apr. 21, 2005

(51) Int. Cl.$^7$ .............................. G01N 1/28; H01J 49/16
(52) U.S. Cl. ..................................... 250/307; 250/288
(58) Field of Search ................................ 250/306, 307, 250/309, 288; 219/121.67, 121.6, 121.68, 121.73, 121.8; 264/400

(56) References Cited

U.S. PATENT DOCUMENTS

| | | | |
|---|---|---|---|
| 3,868,507 A | * | 2/1975 | Panitz ........................ 250/306 |
| 4,329,617 A | | 5/1982 | Littwin |
| 5,440,124 A | | 8/1995 | Kelly et al. |
| 5,475,318 A | * | 12/1995 | Marcus et al. ............... 250/306 |
| 5,633,455 A | * | 5/1997 | Quate ......................... 250/307 |
| 5,779,920 A | | 7/1998 | Chadha et al. |
| 5,780,187 A | | 7/1998 | Pierrat |
| 5,938,493 A | | 8/1999 | Vickers |
| 6,576,900 B2 | * | 6/2003 | Kelly et al. .................. 250/307 |
| 2002/0061418 A1 | | 5/2002 | Imanishi |
| 2002/0177288 A1 | | 11/2002 | Brown et al. |
| 2003/0034093 A1 | | 2/2003 | Morris et al. |
| 2003/0066962 A1 | | 4/2003 | Kaito et al. |
| 2003/0095266 A1 | | 5/2003 | Detalle et al. |
| 2003/0136769 A1 | | 7/2003 | Lin et al. |
| 2004/0056195 A1 | * | 3/2004 | Kuhlman et al. ........... 250/307 |

FOREIGN PATENT DOCUMENTS

WO    WO 99/14793 A1    3/1999

OTHER PUBLICATIONS

Marcus et al., "Formation of silicon tips with <1 nm radius", Applied Physics Letters 56 (3), Jan. 15, 1990, pp. 236–238.*
Imago Scientific Instruments Corporation, "LEAP Atom Probe," 1 page, 2002, <http://www.imago.com>.
Imago Scientific Instruments Corporation, "What is an Atom Probe?" 1 page, 2002, <http://www.imago.com>.
Imago Scientific Instruments Corporation, "Example Applications" 1 page, <http://www.imago.com/mos.html>, 2002.
Cameca, "OTAP Instrument," 1 page, retrieved from the Internet on Aug. 21, 2003, <http://www.cameca.fr.html/product_otap.html>.
Xsil, "xise200 for Vias and micro–machining," 1 page, retrived from the Internet on Aug. 16, 2003, <http://www.xsil.com/products/index.htm>.
Tamarack Scientific Co., Inc., "Excimer Laser Ablation Equipment," 1 page, 2002, retrieved from the Internet on Aug. 16, 2003, <http://www.tamsci.com/products/ablation.html>.

(Continued)

Primary Examiner—Jack I. Berman
(74) Attorney, Agent, or Firm—Perkins Coie LLP (57) ABSTRACT

The present disclosure provides methods for preparing samples for atom probe analysis and methods for analyzing such samples. In one exemplary implementation, a surface of the sample may be positioned with respect to a laser source and laser energy may be directed from the laser source toward the sample surface, removing material from the sample to define an annulus about a sample column. The sample column may be provided with a reduced-diameter apex at its outward end, e.g., by etching. This apex may be juxtaposed with an electrode of an atom probe and material may be selectively removed from the apex for analysis by controlling energy delivered to the apex, e.g., by the electrode.

43 Claims, 4 Drawing Sheets

OTHER PUBLICATIONS

New Wave Research, "Universal Platform Laser Ablation System UP-266," 2 pages, <http://www.new-wave.com>, Mar. 2001.

Miller, et al., "Seeing and Catching Atoms: ORNL's Atom Probe Field Ion Microscope," 6 pages, retrieved from the Internet on May 7, 2003, <http://www.ornl.gov/ORNLReview/rev28-4/text/atoms.htm>.

"Leap Overview," 1 page, retrieved from the Internet on May 7, 2003, <http://analytical.chem.wisc.edu/524class/Folders/Current/LEAPa.html>.

Kuhlman, K.R. et al., "Fabrication of specimens of metaphoric magnetite crystals for field ion microscopy and atom probe microanalysis," Ultramicroscopy, vol. 89, pp. 169-176, 2001, Elsevier Science B.V.

* cited by examiner

METHODS FOR PREPARING SAMPLES FOR ATOM PROBE ANALYSIS

TECHNICAL FIELD

The invention generally relates to analysis of samples with an atom probe. Aspects of the invention have particular utility in connection with preparing samples, e.g., semiconductor wafers or other microelectronic components, for analysis in an atom probe.

BACKGROUND

The properties of some materials can be rather dramatically changed by the presence of relatively small quantities some elements, which may be present as impurities or dopants. For example, the electrical characteristics of a silicon-based semiconductor can be materially altered by the addition of oxygen or dopants such as arsenic or boron. Maintaining both the surface concentration and a concentration gradient of these elements in the semiconductor material within acceptable ranges is important in maintaining consistent product quality.

A variety of analytical techniques have been developed to characterize sample compositions on very small scales. For example, Energy Dispersive X-Ray Spectrometry (EDS) and Wavelength Dispersive X-Ray Spectrometry (WDS) have been used to analyze the surface of a sample in a non-destructive manner. Unfortunately, EDS, WDS and a number of other techniques are unable to reliable quantify material composition as a function of depth from the outer surface.

One analytical technique that does provide a depth profile of a sample's composition employs the use of an atom probe, which is essentially a time-of-flight mass spectrometer. In an atom probe, a surface of a sample is oriented toward, but spaced from, a detector plate. A high intensity electric field is established adjacent the sample surface. This electric field causes field evaporation of the atoms at the surface of the sample and these ionized atoms are drawn toward the detector. The electric field strength can be selectively pulsed for brief periods of time above the field strength necessary to evaporate atoms from the sample surface. This will establish a narrow range of time during which the atoms are released, allowing the time of flight for each atom to be determined for use in identifying the atom. In some atom probes, a local electrode is positioned proximate the sample to better concentrate the electrical field. Such so-called local-electrode atom probes (LEAPs) are discussed, for example, in U.S. Pat. No. 5,440,124, the entirety of which is incorporated herein by reference.

To achieve the required electric field density, the sample desirably has a very short tip that can be positioned immediately proximate the local electrode. The sharp point of this so-call "microtip" typically has a radius of curvature at its apex of less than 300 nm. These microtips may take the form of a sharpened tip at the end of an elongated acicular sample or a projection from a broader sample surface. In the latter sample type, an array of the projections may be arranged across at least a portion of the sample's surface, with each of the projections defining a separately evaporable microtip.

One technique for forming acicular samples involves growing the acicular projections on a substrate, e.g., by selected deposition on an etched wafer. Although this can be useful when attempting to analyze the material which is being deposited, it is of little value in analyzing the composition of an existing structure. Atom probe samples may also be mechanically grooved to form an array of acicular projections. In essence, this involves scribing the surface of the sample to a predetermined depth, e.g., using a diamond scribe or saw. Controlling the scribe or saw with sufficient precision to yield acicular projections of the requisite dimensions can prove quite difficult.

Ion beam mask etching has also been used to produce an array of microtips distributed essentially randomly across a sample surface. In this process, a number of particles of a material with a low sputtering rate, e.g., diamond or alumina particles, are scattered across the sample surface. The sample surface may then be eroded using an ion beam, e.g., by ion sputtering or reactive ion etching. The particles on the surface will shield a portion of the sample, leaving a cone beneath the particle. Continuing the ion beam exposure until the particles are also removed will yield an essentially random array of conical microtips, with each of the microtips being associated with the location of a particle on the original sample surface.

One shortcoming of ion beam mask etching is the difficulty of forming a microtip at a precise location. When examining the composition of an ion-doped area of a silicon wafer, for example, it may be difficult to precisely place a particle on the doped area to form a microtip at that location. Currently, the masking particle typically must be fabricated in place, e.g., using electron beam-fabricated carbon spikes. This relatively time-consuming multi-stage process requires specialized equipment and highly trained operators to yield reproducible results.

DETAILED DESCRIPTION

A. Overview

Various embodiments of the present invention provide methods of preparing samples for atom probe analysis and methods of analyzing a portion of a microelectronic component. The terms "microelectronic component" may encompass a variety of articles of manufacture, including one or more memory modules (e.g., SIMM, DIMM, DRAM, flash-memory), ASICs, processors, semiconductor wafers, semiconductor dies singulated from such wafers, or any of a variety of other types of microelectronic devices or components therefor. The term "atom probe" encompasses a variety of time-of-flight mass spectrometers, including atom probe field ion microscopes, imaging atom probes, wide angle atom probes, and local-electrode atom probes.

One embodiment of the invention provides a method of preparing a sample for atom probe analysis. In accordance with this method, a surface of the sample is positioned with respect to a laser source. Laser energy is directed from the laser source toward the surface to remove material from the sample. Removing the material defines a recessed surface and leaves a projection of sample material projecting beyond the recessed surface. A lateral dimension of at least a portion of the projection is reduced to form a microtip having a reduced-dimension apex spaced from the recessed surface. The microtip may be juxtaposed with an electrode of an atomic probe to facilitate analysis of the sample. In one implementation of this embodiment, removing the material defines a plurality of projections.

A method of analyzing a portion of a sample in accordance with another embodiment involves selectively removing material from the sample with laser energy to define an annulus about a sample column. The sample column is provided with a reduced-diameter apex at its outward end. The apex is juxtaposed with an electrode of an atom probe and, with the apex so juxtaposed, material is selectively removed from the apex by controlling energy delivered to the apex.

Another embodiment of the invention provides an alternative method of analyzing a portion of a sample. In accordance with this embodiment, material is selectively removed from the sample using laser energy to define an array of sample columns including spaced-apart first and second sample columns. Each of the first and second sample columns may be provided with a reduced-diameter apex at its outward end. The apex of the first sample column may be juxtaposed with an electrode of an atom probe and material may be selectively removed from the apex by controlling energy delivered to the apex. In a further adaptation of this embodiment, the relative position of the sample and the electrode may be changed to juxtapose the reduced-diameter apex of the second sample column with the electrode and selectively remove material from the apex of the second sample column.

Still another embodiment of the invention provides a method of analyzing an area of interest of a sample that includes identifying an area of interest on a surface of the sample. Laser energy is directed toward the surface to remove material from the sample at least adjacent the area of interest. Removing the material defines a recessed surface and leaves a projection of sample material at least adjacent the area of interest that projects beyond the recessed surface. The projection may be provided with a reduced-diameter apex at its outward end and the resultant projection may be juxtaposed with an electrode of an atomic probe.

For ease of understanding, the following discussion is broken down into two areas of emphasis. The first section describes embodiments of the invention that provide methods for preparing samples for atom probe analysis. The second section outlines methods of analyzing samples with atom probes according to several embodiments of the invention.

B. Sample Preparation

Figure 1:
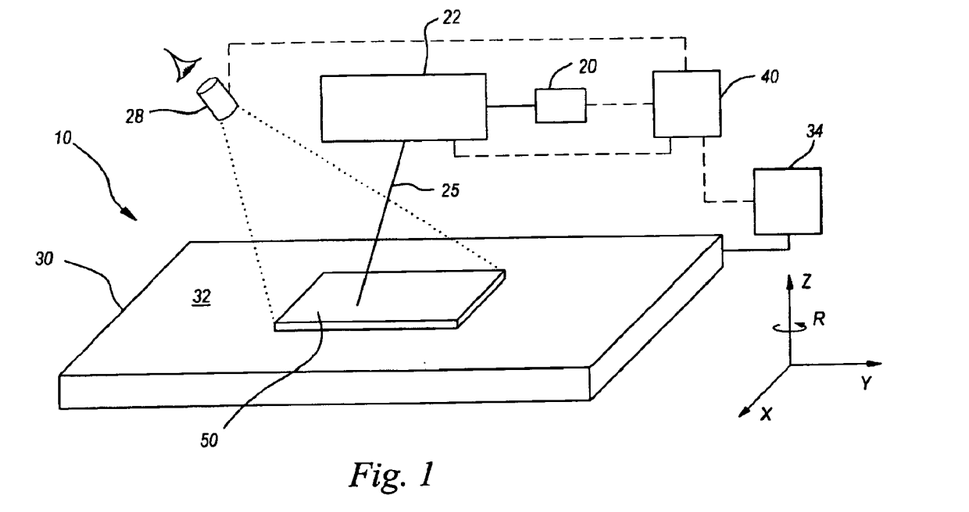
FIG. 1 is a schematic illustration of a laser ablation system that may be used in an embodiment of the invention.

FIG. 1 schematically illustrates a laser processing system 10 that may be used in accordance with embodiments of the invention. Laser processing systems similar to the laser processing system 10 shown in FIG. 1 are well known in the art and need not be explained in great detail here. For example, U.S. Patent Application Publication Nos. 2002/0177288 and 2003/0034093 (the entirety of each of which is incorporated herein by reference) discuss laser processing systems that may be used to cut semiconductor materials. Suitable laser processing systems are also commercially available from a variety of sources, including Tamarack Scientific Co., Inc. of Corona, Calif., U.S.A., and Xsil USA of Loveland, Colo., U.S.A.

Briefly, the laser processing system 10 of FIG. 1 generally includes a laser source 20, a table 30, and a controller 40. The laser source 20 may be operatively coupled to a beam delivery system 22. As is known in the art, such a beam delivery system 22 may employ optical elements (e.g., lenses and/or masks, not shown) to shape and/or direct the laser energy 25 toward a precise location. If so desired, the laser processing station 10 may also include a microscope 28 or the like, which may include a video display, to allow users to view the workpiece.

The table 30 has an upper surface 32 adapted to support a sample 50 for laser processing. The table 30 may be moved by an actuator 34. As is known in the art, such an actuator 34 may be used to translate the table 30 in an X-Y plane, vertically with respect to a Z-axis, or rotationally, as indicated by arrow R in FIG. 1. This will help properly position the sample 50 with respect to the beam delivery system 22 to accurately direct the laser energy 25 to a precise location on the sample 50.

The controller 40 may be operatively coupled to one or more of the laser source 20, beam delivery system 22, and the table actuator 34. In one embodiment, the controller 40 comprises at least one computer having a programmable processor programmed to control operation of these components to selectively remove material from the sample 50, as discussed below.

Figure 2:
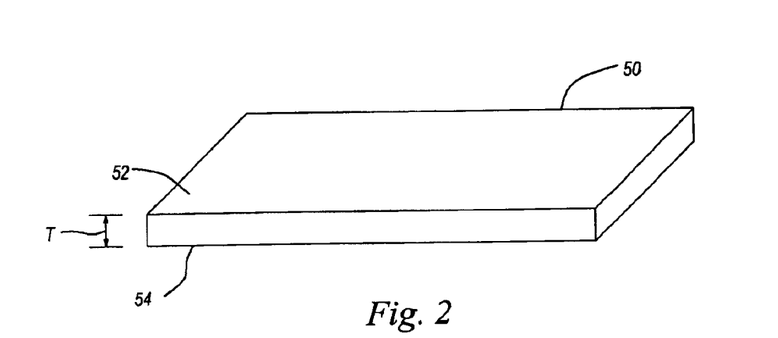
FIG. 2 is a schematic isometric view of a sample to be analyzed.

FIGS. 2–6 schematically illustrate stages in a method of preparing a sample for atom probe analysis in accordance with one embodiment of the invention. FIG. 2 shows a sample 50 having a front surface 52 and a back surface 54. The sample 50 has an initial thickness T between the front and back surfaces 52 and 54. In one embodiment, the sample 50 may be substantially planar, with the front and back surfaces substantially parallel to one another.

The sample 50 may comprise any material of interest that may be removed, e.g., ablated, using a laser. In one particular embodiment, the sample 50 comprises a microelectronic component, e.g., a semiconductor wafer or a semiconductor die.

Figure 3:
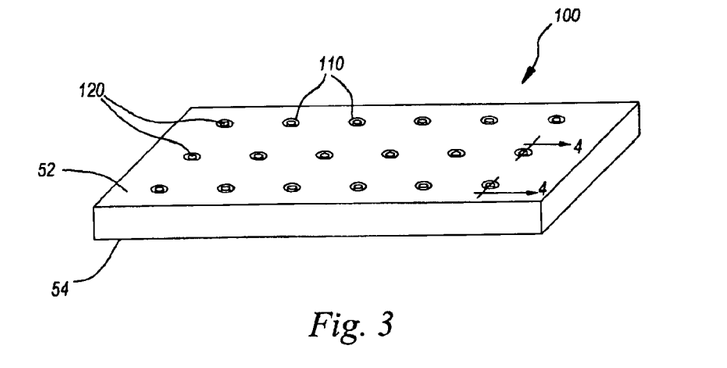
FIG. 3 is a schematic isolation view of the sample of FIG. 2 after removal of an array of annular portions of the sample in accordance with an embodiment of the invention.

FIG. 3 schematically illustrates a laser-processed sample 100 that may be formed from the sample 50 in accordance with one embodiment of the invention. The laser-processed sample 100 may be formed by directing laser energy from the laser source 20 onto the front surface 52 of the sample 50 to remove material from the sample, e.g., by ablation. In one embodiment, the laser energy may essentially scribe the front surface 52, e.g., by tracing a path in the sample material.

In the embodiment shown in FIGS. 3–6, the laser may trace a generally circular path to selectively remove at least one annular volume of material from the sample 50. Removing this annular volume of material will leave a column 120 within an annulus 110. The particular embodiment shown in FIG. 3 has an array of sample columns 120, each being defined by a separate annulus 110. The array of sample columns 120 may be positioned on the sample surface 52 in any suitable arrangement. In the illustrated laser-processed sample 100, the sample columns 120 are arranged in a regular array. Such an arrangement may be useful, for example, to develop a composition profile for a selected area of the sample 50. Most conventional ion beam mask etching processes produce a more random array, which may make plotting a composition profile as a function of position more difficult.

Figure 4:
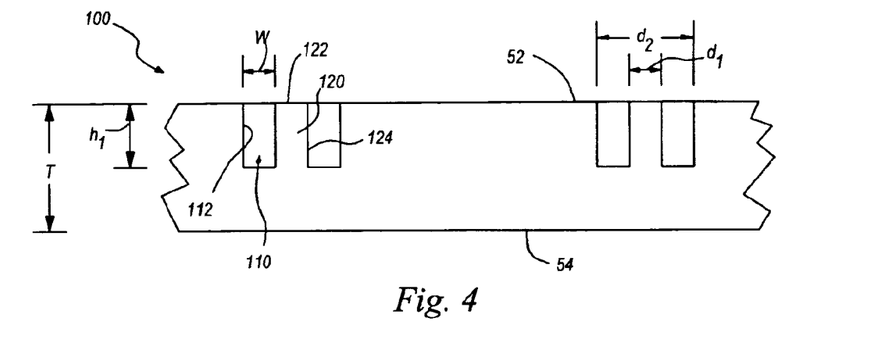
FIG. 4 is a schematic cross-sectional view taken along line 4—4 in FIG. 3.

FIG. 4 shows a portion of the laser-processed sample 100 in greater detail. Each of the annuli 110 in the laser-processed sample 100 has an inner surface that defines a periphery 124 of a sample column 120 and an outer boundary that defines an inward surface 112 of the annulus 110. The inner dimensions of the annulus define the cross-sectional dimensions of the sample column 120. In the illustrated embodiment, the annuli 110 are generally circular and each sample column 120 has a diameter $d_1$. Each annulus also has an outer diameter $d_2$ that is greater than the inner diameter $d_1$. The difference between these two diameters defines an annulus width W between the periphery 124 of the sample column 120 and the inward surface 112 of the annulus 110. Suitable dimensions for the diameters $d_1$ and $d_2$ and the annulus width W may vary depending on the nature of the material and the nature of the atom probe (discussed below) to be used. In one embodiment, the diameter d, of the sample column 120 is substantially constant along its length and may be on the order of about 20 microns or less, e.g., no greater than about 10 microns. The annulus width W between the sample column 120 and the inward surface 112 of the annulus 110 is desirably at least about 10 microns. Annulus widths of 100 microns or greater may be advantageous for some applications.

The annuli 110 in FIG. 3 are substantially circular and have a constant width W, yielding sample columns 120 that are substantially circular in cross-section and substantially centered in the annulus 110. In other embodiments, the annulus 110 can have other, non-circular shapes, e.g., square, rectangular, or elliptical shapes. Similarly, the sample columns 120 may have various cross-sectional shapes, such as squares, rectangles, or ellipses. If so desired, the outer periphery of the annulus (defined by the inward surface 112) may have a different shape than the cross-sectional shape of the sample column, leading to variations in the annulus width W around the periphery 124 of the sample column 120.

As shown in FIG. 4, the annulus 110 extends from the front surface 52 toward the back surface 54 of the laser-processed sample 100, but does not extend through the entire thickness T. The depth of the annulus 110 will largely determine the height $h_1$ of the sample column 120. In the illustrated embodiment, the outer end 122 of the sample column 120 remains substantially coplanar with at least the adjacent portion of the front surface 52 of the laser-processed sample 100. The height $h_1$ of the sample columns 120 will depend, at least in part, on the amount of material removed in forming the apex 132 of the microtip 130 discussed below in connection with FIG. 6. Typical sample column heights on the order of about 25 microns or less, e.g., no greater than about 20 microns, are expected to suffice for many atom probe applications.

In select embodiments of the invention, the sample column 120 may be used as a microtip without forming a smaller-dimension apex. For most atom probes today, though, this would either require that the sample columns 120 be extremely narrow (i.e., have a very small diameter $d_1$) or require an atom probe that is capable of handling a larger microtip apex. In accordance with one embodiment of the invention, therefore, the sample columns 120 may be provided with a reduced-diameter apex (132 in FIG. 6) at its outward end.

Figure 5:
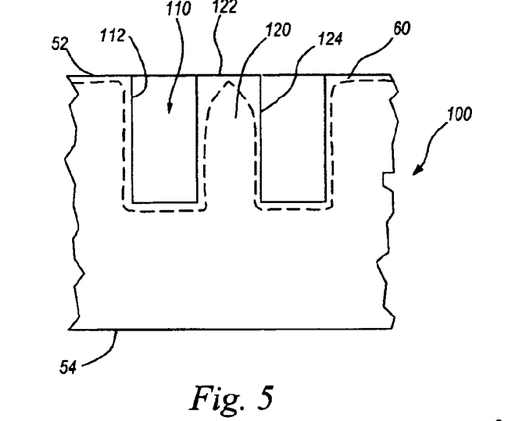
FIG. 5 is a schematic cross-sectional view of a portion of the sample of FIG. 4 after it has been treated with a chemical agent.
Figure 6:
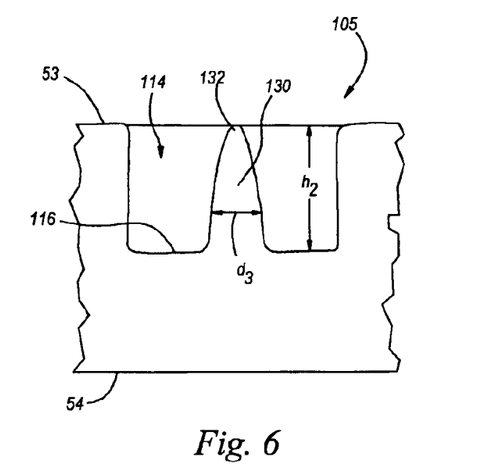
FIG. 6 is a schematic cross-sectional view of the portion of the sample shown in FIG. 5 after selective etching.

FIGS. 5 and 6 schematically illustrate two stages in a process of forming a microtip 130 from the sample column 120 in accordance with one embodiment of the invention. In FIG. 5, the laser-processed sample 110 has been exposed to a reactant that will react with the material of the sample 100, desirably penetrating to a predictable depth beneath the surface of the sample 100. In one embodiment, the original sample 50 may comprise a silicon-based semiconductor wafer and the reactant may comprise oxygen or air. The oxygen will react with the silicon in the semiconductor material to form a reaction byproduct layer 60 of silicon oxide ($SiO_x$) having a reproducible thickness. The oxide layer 60 extends over the front surface 52, the inward surface 112 of the annulus 110, the bottom of the annulus 110, and the periphery 124 and outer end 122 of the sample column 120. As suggested in FIG. 5, the depth to which the oxide layer 60 penetrates may vary from one location to another. In particular, the oxide layer 60 generally will be thicker adjacent sharp corners, e.g., the generally circular junction between the periphery 124 and the outer end 122 of the sample column 120.

In the embodiment illustrated in FIGS. 5 and 6, the layer of the reaction byproduct, in this case the oxide layer 60, can be selectively removed from the laser-processed sample 100 to yield an atom probe sample 105. This may be achieved by etching the surface of the laser-processed sample 100 of FIG. 5 with an etchant that will preferentially etch the reaction byproduct. If the sample 100 is silicon-based with a layer 60 of silicon oxide, for example, hydrofluoric acid is one of a number of etchants known in the art that will selectively etch the silicon oxide faster than it etches the underlying silicon. In one useful embodiment, all of the sample columns 120 formed from the sample 50 may be substantially simultaneously oxidized in one oxidation process and substantially simultaneously etched in one etching process.

In FIG. 6, the oxide layer 60 has been stripped off, leaving a microtip 130. Stripping the oxide layer 60 along the length of the sample column 120 provides the microtip 130 with a somewhat smaller diameter $d_3$ along much of its length, with the diameter of the microtip 130 decreasing as it moves outwardly toward a relatively acute apex 132. Appropriate dimensions for the apex 132 will depend in large part on the nature of the sample material and the capabilities of the atom probe used to analyze the microtip 130. In one embodiment, the apex 132 has a radius of curvature of no greater than about 300 nm, with a radius of curvature on the order of about 10–200 nm, e.g., 50–150 nm, being expected to yield acceptable results for silicon-based semiconductor samples. The removal of the oxide layer 60 may yield a microtip 130 that has a height $h_2$ that is less than the height $h_1$ of the sample column 120 from which it was formed. The difference between the two heights $h_1$ and $h_2$ will depend on the extent of etching at the outer end 122 of the sample column relative to the extent of etching at the recessed surface 116 at the bottom of the etched annulus 114. Microtips 30 having heights $h_2$ on the order of about 20 nanometers or less are expected to work well.

The removal of the layer 60 from the sample 100 of FIG. 5 will also widen the original annulus 110, yielding a somewhat wider etched annulus 114. In one embodiment, this etched annulus 114 is at least about 10 microns wide.

FIGS. 5 and 6 illustrate one particular embodiment of the invention that employs selective etching of a reaction byproduct. Such a two-stage process may enhance control over the etching and the shape of the microtip 130, but will not be necessary in all circumstances. Accordingly, other embodiments of the invention may employ a one-stage etching process wherein the laser-processed sample 100 of FIG. 4 is etched without an intermediate reaction (suggested in FIG. 5).

Figure 7:
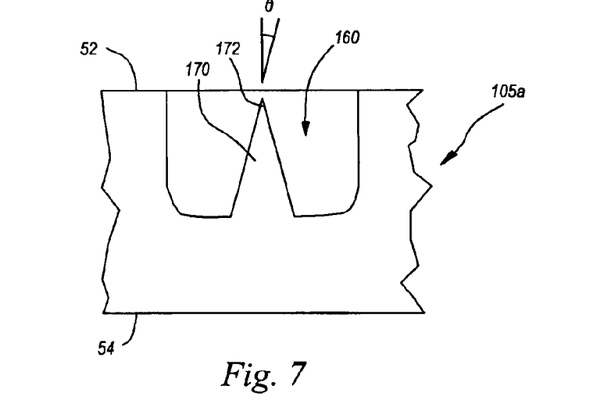
FIG. 7 is a schematic cross-sectional view of a microtip formed in accordance with another embodiment of the invention.

FIG. 7 schematically illustrates an atom probe sample 105a that may be formed from the laser-processed sample 100 of FIG. 4 using an alternative process. Instead of using chemical treatments such as etching, the microtip 170 of FIG. 7 may be formed using a laser processing system, e.g., the laser processing system 10 shown in FIG. 1. In forming the annulus of FIGS. 3 and 4, the beam delivery system 22 may direct the laser energy in a direction substantially normal to the front surface 52 of the sample 50. To form the reduced-dimension apex 172 of the microtip 170 in FIG. 7, the laser energy may be directed at an angle θ of about 5–10° from normal. By rotating the sample table 30 (FIG. 1) and/or the orientation of the laser energy 25 (FIG. 1), the sample column 120 may be sharpened, yielding the reduced-diameter apex 172. The process may also widen or slightly reshape the annulus 110, forming the modified annulus 160 shown in FIG. 7.

In this embodiment, the microtip 170 may be formed in two steps, i.e., first forming a sample column 120 having a substantially constant dimension along its length then, in a subsequent process, reducing the diameter of the sample column 120 adjacent the outer end to form the sharpened apex 172. In one adaptation of this embodiment, the beam delivery system 22 and the controller 40 may be adapted to form the structure shown in FIG. 7 from the sample 50 of FIG. 2 in a single step by simultaneously forming the annulus 160 and the reduced-dimension microtip 170.

As noted above, the sample columns 120 in the laser-processed sample 100 of FIG. 3 are arranged in a substantially regular array. In another embodiment, the position of one or more of the sample columns 120 may be selected by a user to permit analysis of a particular area of interest. In accordance with such an embodiment, a user may identify an area of interest on the front surface 52 of the sample 50, e.g., using the microscope 28 in the laser processing system 10 of FIG. 1. This area of interest may, for example, comprise a particular doped area of a semiconductor sample or an area of the surface 52 that has a different appearance from other areas of the surface 52. Once an area of interest has been identified, laser energy from the laser source 20 may be directed toward the surface 52 by the beam delivery system 22 (FIG. 1) to remove material from the sample at least adjacent the area of interest. For example, the laser energy may form an annulus 110 within the area of interest. If the area of interest is relatively small, the laser energy may circumscribe the area of interest to include the area of interest within the resultant sample column 120. As is known in the art, the operator may control the location at which the laser energy is delivered by using the controller 40 in conjunction with the microscope 28 or other viewing system. This process can be repeated as many times as desired on the sample, yielding a single sample column 120 or an irregular array of sample columns 120, each of which may be positioned adjacent a different area of interest.

Figure 8:
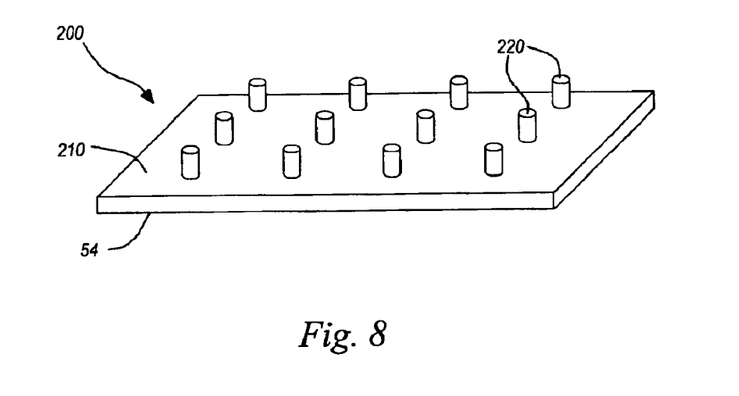
FIG. 8 is a schematic isometric view of the sample of FIG. 2 after laser processing in accordance with an alternative embodiment of the invention.
Figure 9:
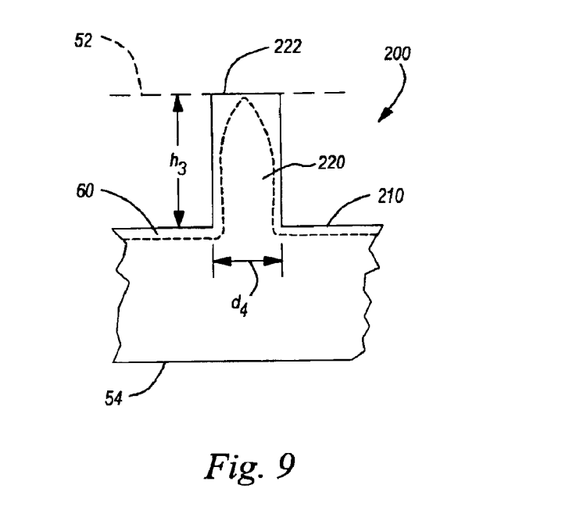
FIG. 9 is a schematic cross-sectional view of a portion of the sample of FIG. 8 after it has been treated with a chemical agent.
Figure 10:
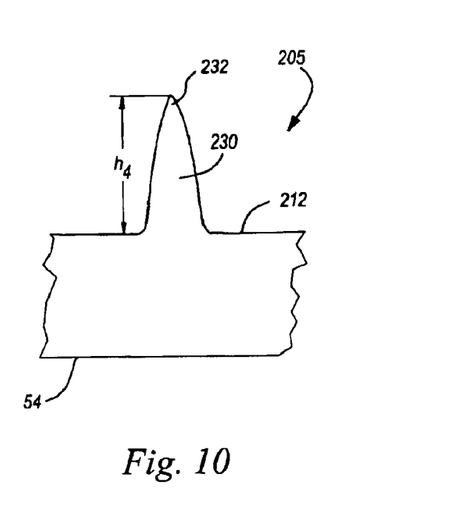
FIG. 10 is a schematic cross-sectional view of the portion of the sample shown in FIG. 9 after selective etching.

FIGS. 8–10 schematically illustrate a method of preparing a sample for atom probe analysis in accordance with another embodiment of the invention. The process of FIGS. 8–10 may start with the same sample 50 illustrated in FIG. 2. Instead of forming an array of annuli 110 to define sample columns 120 in the embodiment of FIGS. 3–6, the laser processing system 10 may remove a bulk of the material between adjacent sample columns 220. This will produce an array of sample columns 220 projecting outwardly from a common recessed surface 210. If so desired, the recessed surface 210 may be generally planar.

Although the sample columns 220 may have differing heights, in one embodiment the outer ends 222 (FIG. 9) of the sample columns 220 comprise a portion of the front surface 52 of the original sample 50 (FIG. 2). If the original sample 50 was substantially planar and the recessed surface 210 is substantially planar and parallel to the original front surface 52, each of the sample columns 220 will have approximately the same height $h_3$. Although the sample columns 220 may have differing sizes or shapes, each of the sample columns 220 in the illustrated embodiment is generally circular in cross-section and has a diameter $d_4$. Suitable diameters $d_4$ for the sample columns 220 may be about the same as suitable diameters $d_1$ (FIG. 4) for the sample columns 120 discussed above.

FIGS. 9 and 10 illustrate stages in a process analogous to that illustrated in FIGS. 5 and 6 discussed above. In particular, the laser-processed sample 200 of FIG. 8 may be exposed to an agent that will react with the material of the sample 100 and penetrate to a predictable depth. If the laser-processed sample 200 comprises silicon, for example, reacting the silicon with oxygen (e.g., by heating in air) will yield a reaction byproduct layer 60 of silicon oxide. The layer 60 may be selectively removed, e.g., by etching with HF. As shown in FIG. 10, this will produce an atom probe sample 205 having an etched surface 212, which may be generally planar, with a series of microtips 230 projecting outwardly from the surface 212. Each of the microtips 230 have a reduced diameter apex 232 and a microtip height $h_4$, which may be about the same as the height $h_3$ of the sample column 220. Suitable microtip heights $h_4$ and radii of curvature for the apex 232 may be substantially the same as the microtip height $h_2$ and radius of curvature of the apex 132 discussed above in connection with FIG. 6.

As with the preceding embodiment, the microtips 230 need not be formed using such a two-stage etching process. In one embodiment, for example, the sample is not reacted to form the reaction byproduct layer 60. Instead, the sample columns 220 of FIG. 8 may be etched to yield the microtips 230 shown in FIG. 10. Alternatively, the microtips 230 may be formed simultaneously with forming the recessed surface 210, e.g., by controlling an angle of incidence of the laser energy, as discussed above in connection with FIG. 7.

C. Sample Analysis

Figure 11:
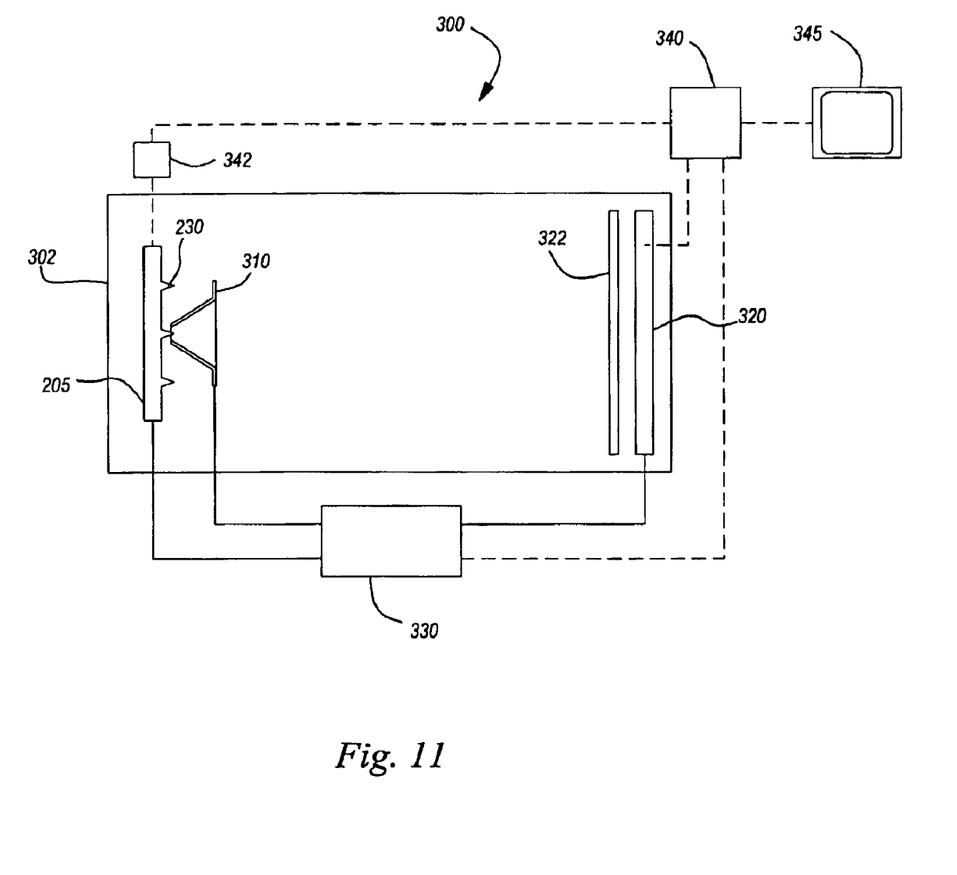
FIG. 11 is a schematic illustration of a scanning atom probe which may be used in an embodiment of the invention.

FIG. 11 schematically illustrates aspects of an atom probe 300 that may be used in accordance with embodiments of the invention. Atom probes are well known in the art and are commercially available from a number of suppliers, including Cameca Instruments Inc. of Trumbull, Conn., USA, and Imago Scientific Instruments Corporation of Madison, Wis., USA. Accordingly, atom probes need not be discussed in great detail here.

Briefly, though, the atom probe 300 of FIG. 11 includes a vacuum chamber 302 that may enclose an atom probe sample (typified in FIG. 11 as the atom probe sample 205 of FIG. 10), a local electrode 310, and a detector plate 320. A high voltage power supply 330 may be operatively coupled to the sample 205 and the local electrode 310 to generate a high voltage electric field adjacent the apex of the microtip 230 of the sample 205. The power supply 330 may also be coupled to the detector plate 320 to establish an applied electric field gradient between the sample 205 and the detector plate 320. As is known in the art, a microchannel plate 322 may be disposed between the sample 205 and the detector plate 320.

A controller 340 may be operatively coupled to the power supply 330 and the detector plate 320. The controller 340 may also be operatively coupled to a temperature monitor 342 adapted to monitor a temperature adjacent the apex of the microtip under analysis. The controller 340 may comprise one or more computers programmed to control operation of the power supply 330 and temperature monitor 342 and to collect information from the detector plate 320.

In use, a microtip 230 of the sample 205 may be positioned proximate a small aperture in the local electrode 310. By appropriate control of the electric field adjacent the microtip 230, atoms on the microtip's surface may be ionized, essentially one atom at a time. After leaving the atom probe sample 205, the ionized atom may be pulled toward the detector plate 320 by the applied electric field gradient. The detector plate 320 is adapted to record the location and time of impact of the atom. Knowing the location of the impact will help pinpoint the location of the atom on the microtip 230 and the time of impact can be correlated to the mass of the atom, and hence to the identity of the atom. The data collected by the detector plate 320 may be communicated to the processor 340. In one embodiment, the processor 340 may display a graphical representation of the composition of the microtip 230 on a display 345.

As noted above, some embodiments of the invention provide atom probe samples (e.g., atom probe sample 205) that include multiple microtips (e.g., microtips 230). Once a first microtip 230 of such a sample 205 has been analyzed, analysis in accordance with a further embodiment of the invention proceeds by moving the sample 205 and/or the electrode 310 to juxtapose a second microtip 230 proximate the electrode 310. The electric field adjacent the second microtip 230 may be controlled to analyze the composition of the second microtip 230 in much the same fashion as the first microtip 230. This process may be continued for each of the microtips 230 formed on the sample 205.

Embodiments of the invention provide material advantages over some of the more conventional approaches to preparing atom probe samples. For example, as noted above, ion beam mask etching tends to form an essentially random array of microtips. This can make plotting a composition profile over an area of the sample more difficult. Ion beam mask etching also limits the ability to pinpoint a particular area of interest on the sample surface for analysis. In contrast, embodiments of the present invention allow fairly precise control over the location and dimensions of microtips (e.g., 130 in FIG. 6 or 230 in FIG. 10) on a sample surface 52. It is also anticipated that embodiments of the invention may allow atom probe samples to be formed more rapidly and more cost effectively than may otherwise be achieved using ion beam mask etching or the like.

The above-detailed embodiments and examples are intended to be illustrative, not exhaustive, and those skilled in the art will recognize that various equivalent modifications are possible within the scope of the invention. For example, whereas steps are presented in a given order, alternative embodiments may perform steps in a different order. The various embodiments described herein can be combined to provide further embodiments.

In general, the terms used in the following claims should not be construed to limit the invention to the specific embodiments disclosed in the specification unless the preceding description explicitly defines such terms. The inventors reserve the right to add additional claims after filing the application to pursue additional claim forms for other aspects of the invention.

What is claimed is:

1. A method of preparing a sample for atom probe analysis, comprising:
    positioning a surface of the sample with respect to a laser source;
    directing laser energy from the laser source toward the surface to remove material from the sample, removing the material defining a recessed surface and leaving a projection of sample material projecting beyond the recessed surface;
    reducing a lateral dimension of at least a portion of the projection projecting from the recessed surface without laser energy to form a microtip having a reduced-dimension apex spaced from the recessed surface; and
    juxtaposing the microtip with an electrode of an atomic probe.

2. The method of claim 1 wherein directing the laser energy comprises tracing a path in the material with the laser energy.

3. The method of claim 1 wherein the recessed surface extends laterally at least about 10 $\mu$m from a periphery of the projection.

4. The method of claim 1 wherein the projection is a first projection and removing material from the sample further defines a regular array of projections.

5. The method of claim 1 wherein the projection is a first projection and removing material from the sample further defines a second projection spaced from the first projection.

6. The method of claim 1 wherein the projection is a first projection, the microtip is a first microtip, and removing material from the sample further defines a second projection spaced from the first projection, the method further comprising reducing a lateral dimension of at least a portion of the second projection to yield a second microtip.

7. The method of claim 6 wherein the apex of the first microtip projects a first distance from the recessed surface and the apex of the second microtip projects a second distance from the recessed surface, the second distance being approximately equal to the first distance.

8. The method of claim 1 wherein removing the material from the sample comprises scribing an annulus about the projection with the laser energy, an outer end of the projection being approximately coplanar with a remaining portion of the sample surface.

9. The method of claim 1 wherein reducing the lateral dimension comprises etching the projection.

10. The method of claim 1 further comprising forming a reaction byproduct layer on the projection and reducing the lateral dimension comprises selectively removing the reaction byproduct layer.

11. The method of claim 1 wherein the sample comprises silicon and the method further comprises oxidizing the projection to form a silicon oxide (SiOx) layer and reducing the lateral dimension comprises selectively etching the silicon oxide.

12. The method of claim 1 further comprising inspecting the sample surface to identify an area of interest, wherein the material is removed from a location that is at least proximate the area of interest.

13. A method of analyzing a portion of a sample, comprising:
    selectively removing material from the sample with laser energy to define an annulus about a sample column;

providing the sample column at least partially surrounded by the annulus with a reduced-diameter apex at its outward end without laser energy;

juxtaposing the apex with an electrode of an atom probe; and with the apex juxtaposed with the electrode, controlling energy delivered to the apex to selectively remove material from the apex.

14. The method of claim 13 wherein selectively removing material to define the annulus comprises tracing a path in the material with the laser energy.

15. The method of claim 13 wherein the annulus has an inner dimension and an outer dimension that is greater than the inner dimension to define a transverse annulus width between the inner and outer dimensions of at least about 10 $\mu$m.

16. The method of claim 13 wherein the sample column is provided with the reduced-diameter apex by etching.

17. The method of claim 13 further comprising forming a reaction byproduct layer on the sample column, wherein the sample column is provided with the reduced-diameter apex by selectively removing the reaction byproduct layer.

18. The method of claim 13 wherein the sample comprises silicon and the method further comprises oxidizing the sample column to form a silicon oxide (SiOx) layer, wherein the sample column is provided with the reduced-diameter apex by selectively etching the silicon oxide.

19. The method of claim 13 wherein the annulus is a first annulus, further comprising selectively removing a second annulus of material from the microelectronic component using the laser energy, the second annulus being spaced from the first annulus.

20. The method of claim 13 wherein the annulus is a first annulus and the sample column is a first sample column, further comprising selectively removing a second annulus of material from the microelectronic component using laser energy to define a second column, the second column being spaced from the first column.

21. The method of claim 20 further comprising providing the second sample column with a reduced-diameter apex substantially simultaneously with providing the first sample column with a reduced-diameter apex.

22. The method of claim 20 further comprising providing the second sample column with a reduced-diameter apex and, after juxtaposing the apex of the first sample column with the electrode, juxtaposing the apex of the second sample column with the electrode.

23. The method of claim 20 further comprising providing the second sample column with a reduced-diameter apex, the apexes being provided on the first and second sample columns by substantially simultaneously etching the first and second columns.

24. The method of claim 13 further comprising inspecting a surface of the sample to identify an area of interest, wherein the sample column is at least proximate the area of interest.

25. A method of analyzing a portion of a sample, comprising:

inspecting a surface of the sample to identify an area of interest;

selectively removing material from the sample using laser energy to define an array of sample columns including a first sample column and a second sample column, the first sample column being spaced from the second sample column and at least proximate the area of interest;

providing the first sample column with a reduced-diameter first apex at its outward end without laser energy;

providing the second sample column with a reduced-diameter second apex at its outward end without laser energy;

juxtaposing the first apex of the first sample column on the sample with an electrode of an atom probe; and with the first apex juxtaposed with the electrode, controlling energy delivered to the first apex to selectively remove material from the first apex.

26. The method of claim 25 further comprising juxtaposing the second apex with the electrode and, with the second apex juxtaposed with the electrode, controlling energy delivered to the second apex to selectively remove material from the second apex.

27. The method of claim 25 wherein the removing material from the sample to define the array comprises removing a plurality of annuli including a first annulus and a second annulus, the first annulus circumscribing the first sample column and the second annulus circumscribing the second sample column.

28. The method of claim 25 wherein the first sample column is provided with the reduced-diameter apex by etching.

29. The method of claim 25 further comprising forming a reaction byproduct layer on the first sample column, wherein the first sample column is provided with the reduced-diameter apex by selectively removing the reaction byproduct layer.

30. The method of claim 25 wherein the sample comprises silicon and the method further comprises oxidizing the first sample column to form a silicon oxide (SiOx) layer, wherein the first sample column is provided with the reduced-diameter apex by selectively etching the silicon oxide.

31. The method of claim 25 wherein the second sample column is provided with the second apex substantially simultaneously with providing the first sample column with the first apex.

32. The method of claim 25 wherein the first sample column is provided with the first apex and the second sample column is provided with the second apex by substantially simultaneously etching the first and second sample columns.

33. A method of analyzing an area of interest of a sample, comprising;

identifying an area of interest on a surface of the sample;

directing laser energy toward the surface to remove material from the sample at least adjacent the area of interest, removing the material defining a recessed surface and leaving a projection of sample material at least adjacent the area of interest projecting beyond the recessed surface;

providing the projection with a reduced-diameter apex at its outward end without laser energy; and juxtaposing the projection with an electrode of an atomic probe.

34. The method of claim 33 wherein directing the laser energy comprises tracing a path in the material with the laser energy.

35. The method of claim 33 wherein the recessed surface extends laterally at least about 10 $\mu$m from a periphery of the projection.

36. The method of claim 33 wherein the projection is a first projection and removing material from the sample further defines a regular array of projections.

37. The method of claim 33 wherein the projection is a first projection and removing material from the sample further defines a second projection spaced from the first projection.

38. The method of claim 37 further comprising providing the second projection with a reduced-diameter apex at its outward end.

39. The method of claim 38 wherein the apex of the first projection is spaced a first distance from the recessed surface and the apex of the second projection is spaced a second distance from the recessed surface, the second distance being approximately equal to the first distance.

40. The method of claim 33 wherein removing the material from the sample comprises scribing an annulus about the projection with the laser energy, an outer end of the projection being approximately coplanar with a remaining portion of the sample surface.

41. The method of claim 33 wherein providing the projection with the reduced-diameter apex comprises etching the projection.

42. The method of claim 33 further comprising forming a reaction byproduct layer on the projection and providing the projection with the reduced-diameter apex comprises selectively removing the reaction byproduct layer.

43. The method of claim 33 wherein the sample comprises silicon and the method further comprises oxidizing the projection to form a silicon oxide (SiOx) layer and providing the projection with the reduced-diameter apex comprises selectively etching the silicon oxide.

* * * * *